United States Statutory Invention Registration [19]

[11] Reg. Number: H71

Sorenson et al.

[45] Published: Jun. 3, 1986

[54] APPARATUS AND METHOD FOR INDICATION OF IONTOPHORETIC DRUG DISPENSER OPERABILITY

[75] Inventors: Paul D. Sorenson, Blaine; Gary A. Lattin, Forest Lake, both of, MN

[73] Assignee: Medtronic, Inc., Minneapolis, Minn.

[21] Appl. No.: 637,643

[22] Filed: Aug. 3, 1984

[51] Int. Cl.[4] ..... A61N 1/30
[52] U.S. Cl. ..... 604/20; 128/783
[58] Field of Search ..... 128/734, 783; 604/20

[56] References Cited

U.S. PATENT DOCUMENTS 3,870,034 3/1975 James ..... 128/734
4,109,645 8/1978 Bacchelli ..... 128/734

OTHER PUBLICATIONS

S. Kaul, "Skin Resistance Biofeedback", *Elektor*, July/August 1980, pp. 7–29.

*Primary Examiner*—John F. Terapane
*Assistant Examiner*—Eric Jorgensen
*Attorney, Agent, or Firm*—John L. Rooney; Joseph F. Breimayer

[57] ABSTRACT

An iontrophoretic medical device has a first light of controlled brightness. Iontophoretic contact with skin is measured by current flow and a second light is illuminated in proportion to current flow. Generally, equivalent brightness of the two lights indicates successful iontophoretic contact.

4 Claims, 3 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

APPARATUS AND METHOD FOR INDICATION OF IONTOPHORETIC DRUG DISPENSER OPERABILITY

BACKGROUND OF THE INVENTION

Field of the Invention—This invention relates to indicators for the degree of iontophoretic contact between iontophoresis device and the skin.

Priot Art—A number of devices have used iontophoresis for delivery of drugs through the skin. For example, the Medtronic CF indicator TM Sweat Test employs iontophoresis to drive pilocarpine to the skin to induce sweat. The sweat is used in the test for cystic fibrosis.

Practitioners using sweat test devices need an indication of when sufficient sweat is collected so that a test can be accurately conducted. Many factors can influence amount of sweat produced during the iontophoretic application of pilocarpine. One of the most influentical factors is the impedance of the interface between the skin and the drug delivery electrode. Skin impedance varies from patient to patient depending on factors such as race, age, skin condition, or metabolic activity.

High skin impedance may often be dramatically lowered by a proper skin preparation, such as scrubbing. The degree of need for such extra scrubbing varies among individuals. If a test fails due to the need for greater skin preparation, it is advantageous to provide an indicator which will alert the practitioner to the need for additional skin preparation before the test is run.

Various methods have been tried to indicate to the operator the quality of the contact. For example, the model 417 Skin Chloride Measuring System produced by Orion Research includes an analog meter with a scale to indicate a zone of appropriate skin impedance which is to be achieved before beginning the manual timing of iontophoretic drug delivery. The needle on the meter is read by the operator to determine when the apparatus may be used.

U.S. Pat. No. 4,109,645 by Bacchelli discloses an instrument for measuring body resistance to ion flow after an established period which allows for the stabilization of skin impedance. This device also gives an analog meter reading for the assessment of impedance.

The analog meters are to cumbersome for quickly indicating to an operator of an iontophoretic device that proper skin preparation has been achieved. Such methods add to the circuit complexity and cost of the device. In the testing for cystic fibrosis, a simple indication is needed that sufficient sweat may be produced as the test is initiated.

SUMMARY OF THE INVENTION

An iontophoretic device constructed according to the present invention includes indicator lights to give a "go" condition indicative of sufficient iontophoretic contact. A control light is provided which serves a dual purpose. Illumination of the control light indicates that adequate power supply voltage is present to power the iontophoretic drug dispenser. Secondly, the control light, when lighted, provides a preset controlled brightness. Means are provided for iontophoretic contact with the skin. For example, this could be iontophoretic delivery of a drug. One example is the delivery of pilocarpine to generate sweat. Means are provided to sense the quality of the iontophoretic contact, preferably by sensing current flow across the skin impedance. Means are provided for determining whether current flow at the skin impedance is adequate. A second light is illuminated in a gradually brightening fashion to indicate the quality of the current flow. As current flow indicates that skin preparation is proper and iontophoretic delivery is achievable, a second light is illuminated to generally equivalent brightness to the control brightness of the first light.

The operator can easily determine by visual inspection of the first and second lights whether iontophoretic contact is sufficient. This indicator avoids the complex meter reading of the prior art systems and gives an indication which is easy to interpret. The operator of the device has an easy "go" or "no go" indication to use in deciding whether drug delivery is occurring in a satisfactory manner.

DETAILED DESCRIPTION OF THE PREFERRED EMBODIMENT

Figure 1:
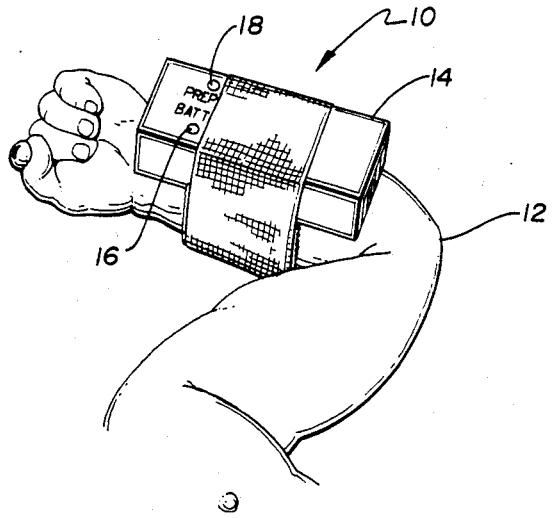
FIG. 1 is a perspective view of an iontophoretic device having an indicator constructed according to the present invention.

A device 10, as illustrated, includes indicator means constructed according to the present invention. Iontophoretic device 10 is illustrated mounted on a patient's arm 12 for iontophoretic delivery of a drug through the skin. The particular drug delivery device illustrated is a Medtronic® CF Indicator TM Sweat Test device which delivers pilocarpine as the first step in a test. On the housing 14 of device 10 are located a first LED or battery indicator light 16 and a second LED or prep light 18.

The use of this sweat test device illustrates the present invention. The skin of the patient is prepared by washing. The device 10 is then strapped to arm 12 and activated. If there is sufficient power to drive device 10, the first LED 16 lights up indicating that the device is operable. First LED 16 blinks on and off during iontophoretic drug delivery.

The physician employing device 10 then inspects second LED 18. As current is conducted across the electrical load consisting of the patient's skin, second LED 18 is illuminated. If skin impedance is sufficiently low to allow proper operation of device 10, second LED 18 is fully illuminated. The physican compares second LED 18 with first LED 16 to determine that skin impedance is sufficiently low to perform a test. If second LED 18 is dimmer than first LED 16, the physician is warned that skin impedance many be too high to perform a successful test.

The normal procedure is then to remove device 10 from arm 12 and reprep the skin. This usually entails scrubbing the area to allow cleaner contact with device 10. The device 10 is then restrapped to arm 12 and the procedure of comparing second LED 18 to first LED 16 is repeated.

Figure 2:
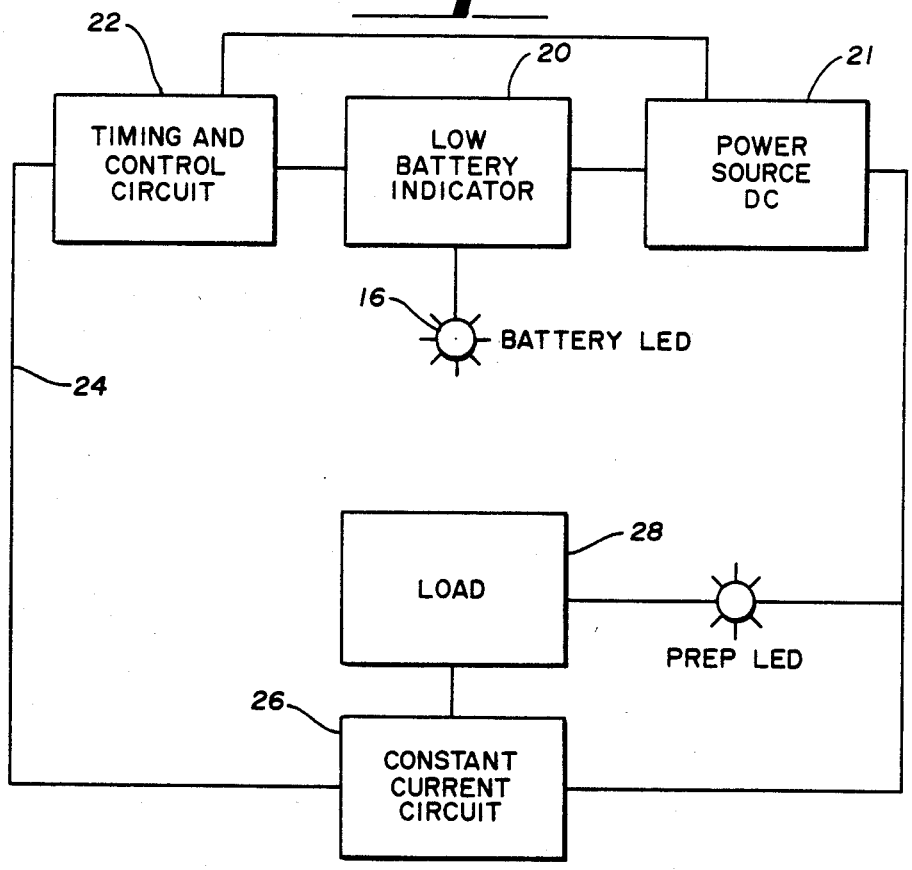
FIG. 2 is a block diagram illustrating an embodiment of the present invention.

The electrical circuit of device 10 is schematically illustrated in FIG. 2. Low battery indicator 20 includes circuitry for sensing voltage of power source 21 of device 10. Low battery indicator 20 controls the illumination of first LED 16 and indicates that there is sufficient power to perform a test. Timing and control circuit 22 provides a control signal which is transmitted on line 24 to constant current circuit 26.

Constant current circuit 26 provides the electrical current to perform iontophoresis on the skin of the patient which is represented by load 28. The resistance across load 28 is in this example, the skin impedance of the patient. LED 18 is in series with load 28 so that its illumination depends upon the resistance of load 28.

Figure 3:
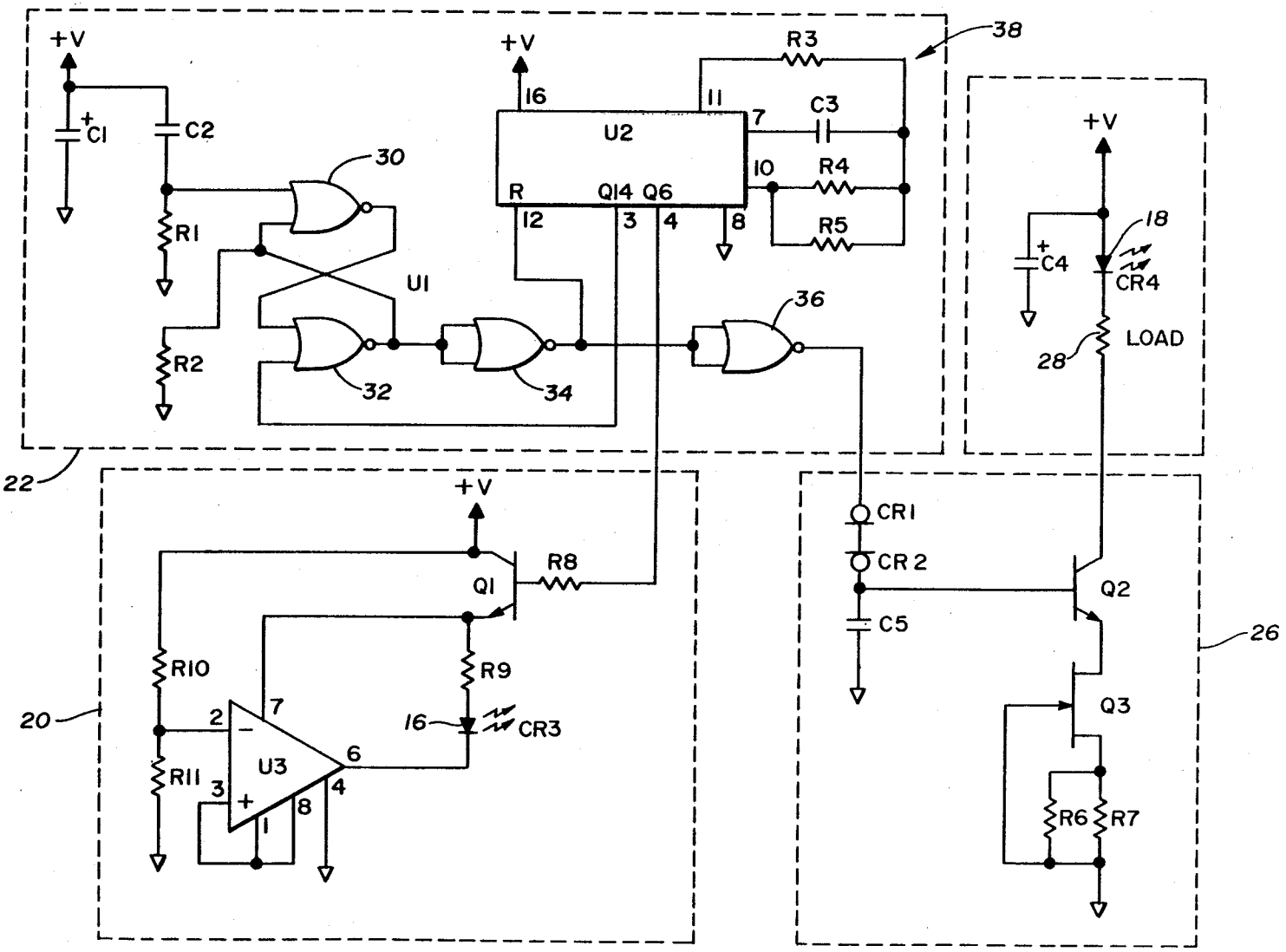
FIG. 3 is a circuit diagram of the system of FIG. 2.

Details of the circuit illustrated in the schematic of FIG. 2 are shown in FIG. 3.

Timing and control circuit 22 comprises 33 microfarad capacitor C1, 01 microfarad capacitor C2, 1 megaohm resistors R1 and R2, NOR gates 30 through 36, 910 kilohm resistor R5, 560 kilohm resistor R4, 0.056 microfarad capacitor C3, 3.3. megohm resistor R3 and ripple counter U2.

Capacitor C1 is connected between ground and the positive 5 volt voltage terminal. This is a filter capacitor whose purpose is to reduce circuit noise, and is not otherwise actively involved in the timing control function. Capacitor C2 is connected between the high voltage side of capacitor C1 and the upper input terminal to NOR gate 30, which terminal is also connected to ground through resistor R1. NOR gates 30 and 32 are coupled in a standard configuration for a flip-flop circuit. That is, the output of NOR gate 30 is connected to the upper input of NOR gate 32, while the output of NOR gate 32 is connected to the lower input to gate 30. The lower input to gate 32 is connected to the counter output Q14 of ripple counter U2. The output of NOR gate 32 is also connected to the two inputs of NOR gate 34. The lower input of gate 30 is also connected to ground through resistor R2. The output of NOR gate 34 is connected to the reset input R of ripple counter U2 and also to both inputs of NOR gate 36. Resistors R4 and R5 are connected in parallel between pin 10 of ripple counter U2 and one side of capacitor C3, which is also connected through resistor R3 to pin 11 of ripple counter U2. The other side of capacitor C3 is connected to pin 9 of ripple counter U2. Pin 8 of ripple counter U2 is connected to ground while pin 16 is connected to the +5 volt power supply. Ripple counter U2 is a CD4060 ripple counter divider available from RCA Solid State Division, Box 3200, Summerville, N.J. 08876. The output of NOR gate 36 is applied to constant current circuit 26 which is described below.

When the device is activated, the inputs to NOR gate 34 will be at a logic "0" since they are connected to ground through resistor R2, and no current is initially flowing in the line. The output of gate 34 will thus be a logic "1" which resets ripple counter U2, setting the Q14 output to a logic "0", and thus the lower input to gate 32 to a logic "0". At the same time a current will begin flowing in the circuit through resistor R1 to ground (charge will be building on capacitor C2) which will set the upper terminal to NOR gate 30 at a logic "1". The output of gate 30 is thus forced to a logic "0" which is applied to the upper input of gate 32. The two inputs to gate 32 being a logic "0", the output will switch to a logic "1". This causes the output of gate 34 to go to a logic "0", which releases the reset on ripple counter U2, which permits it to begin counting, and at the same time causes the output of gate 36 to switch from a logic "0" to a logic "1". While ripple counter U2 is counting the upper input to NOR gate 30 falls to a logic "0", however the output of the gate is maintained at a logic "0" because the lower input to the gate is held at a logic "1" as long as the lower input of gate 32 is held to a logic "0".

Ripple counter U2 is driven by oscillator circuit 38 consisting of resistors R3, R4, R5 and capacitor C3. The value of resistor R5 is selected so that the oscillation period is 36.6 milliseconds. The ripple counter will count the 36.6 milliseconds oscillations so that within approximately 5 minutes its fourteenth counter is triggered, and the Q14 pin goes to a logic "1". This logic "1" signal applied to the lower input of gate 32 causes the output of the gate to go to a logic "0", which in turn forces the output of gate 34 to a logic "1", which holds ripple counter U2 reset and changes the output of NOR gate 36 to a logic "0". The logic "0" output of NOR gate 32 is also applied to the lower input of NOR gate 30. Both inputs of NOR gate 30 being a logic "0", the output will become a logic "1", which is applied to the upper input of NOR gate 32 forcing its output to a logic "0" thereby latching gates 30 and 32 in the "off" state such that the output of NOR gate 36 remains a logic "0" until the cycle is restarted. Thus, timing and control circuit 22 provides a logic "1" signal to constant current circuit 26 for a 5-minute period. While counter U2 is counting up to five minutes, its sixth counter stage will go to a logic "1" approximately every 2.3 seconds. The output of the sixth counter stage (pin 4) will thus go to a logic "1" for a 1.15 second period every 2.3 seconds. This signal is passed to low battery indicator circuit 20. When the counter has fully counted the five minutes and gates 30 and 32 are latched into the "off" state all counter outputs will be at a logic "0" thus holding the various subcircuits in an off position as will be further described below.

Constant current circuit 26 includes two constant current IN5290 diodes CR1 and CR2, 330 microfarad capacitor C5, 2N2222 transistor Q2, 2N4341 FET Q3, 680 kilohm resistor R6 and 510 kilohm resistor R7.

The anode of constant current diode CR1 is connected to the output of NOR gate 36 in timing and control circuit 22. The cathode of diode CR1 is connected to the cathode of diode CR2 while the anode of diode CR2 is connected to one side of capacitor C5 and also to the base of transistor Q2. The other side of capacitor C5 is connected to ground. The emitter of transistor Q2 is connected to the drain of FET Q3. The gate of FET Q3 is connected to ground and is also connected to its own source through parallel resistors R6 and R7. The collector of transistor Q2 is connected to load 28.

When timing and control circuit 22 causes NOR gate 36 to go to a logic "1" state, a 5 volt signal is applied to the anode of diode CR1. Since this is a constant current diode the current that passes through it is fixed and thus the charge on capacitor C5 is built up slowly, over a period of about 1 second. Thus, the voltage applied to the base of transistor Q2 builds up slowly, to the full 5 volt value over the same period, causing the transistor to turn on slowly over the same period. FET Q3 and resistors R6 and R7 form a conventional current-limiting circuit. Resistors are chosen to limit the current to 2 milliamps. Thus, upon application of the signal from timing and control circuit 22, constant current circuit 26 slowly, over a period of about a second, ramps up the current through its output line from 0 to a maximum constant current of 2 milliamps. When, at the end of the 5-minute period, the signal from timing and control circuit 22 drops to a logic "0", the charge on capacitor C5 will slowly drain through current-limiting diode CR2, again over about a 1-second period. Thus, the transistor Q2 will be slowly turned off over the same period and the current through the output line will slowly ramp down to a 0 value.

Low battery indicator circuit 20 comprises 100 kilohm resistor R8, 2N2222 transistor Q1, 2.2 kilohm resistor R9, LED CR3, an LM1OH differential amplifier U3, which is available from National Semiconductor Corp. at 29000 Semiconductor Drive, Santa Clara, CA 95051, 820 kilohm resistor R10 and 12 kilohm resistor R11. The base of transistor Q1 is connected to the Q6 output (pin 4) of ripple counter U2 in timing and control circuit 22 through resistor R8. The collector of transistor Q1 is connected to the positive 17 volt power source and to ground through resistors R10 and R11. The emitter of transistor Q1 is connected to the output (pin 6) of amplifier U3 through resistor R9 and LED CR3, and is also connected to pin 7 of amplifier U3. The value of R9 is selected such that the current passing through it is equal to a minimum desired iontophoretic current level, which is 1.5 ma in the preferred embodiment. Therefore, a current of 1.5 ma flows through LED CR3 which causes CR3 to provide a reference brightness to which the brightness of LED CR4 is visually compared. The negative input terminal (pin 2) of amplifier U3 is connected to the line between resistors R10 and R11. The positive input terminal (pin 3) of amplifier U3 is connected to both pin 1 and pin 8 of the same amplifier. The input pin 4 of the amplifier U3 is connected to ground.

As discussed above, the Q6 output of ripple counter U2 in timing and control circuit 22 will go to a logic "1" for a 1.15 second period once each 2.3 seconds while the counter is running. Each time it goes to a logic "1" transistor Q1 is turned on for the 1.15 second period provided the battery level is above the predetermined level which for this embodiment is 14 volts. The circuit consisting of amplifier U3, resistors R9, R10, and R11 and LED CR3 is a conventional battery-level test circuit disclosed in the applications manual for the U3 amplifier published by National Semiconductor Corporation.

When transistor Q1 turns on, it activates amplfier U3 which compares the voltages between its negative and positive inputs. If the battery voltage is higher than 14 volts the amplifier connects its No. 6 pin output terminal to ground. This closes the circuit from the positive terminal to ground through LED CR3, causing the LED to operate. If the battery voltage is below 14 volts, amplifier U3 will not connect its output (pin 6) to ground and LED CR3 will not turn on. Thus, Low Battery Indicator Circuit 20 will cause LED CR3 to blink at 2.3 second intervals during the 5-minute period when the current is on, providing the battery level is above 14 volts.

Load 28 is illustrated as a resistor connected in series with constant current circuit 26. PREP LED 18 (CR4) is connected in series between the load 28 and a 17 volt power source. A capacitor C4 is connected from the 17 volt power source to ground.

The iontophoretic current flowing through load 28 is inversely proportional to the magnitude of the resistive impedance of load 28. Since the load current must also flow through CR4, the brightness of CR4 is therefore inversely related to the resistance in load 28. A brightness of CR4 less than that of CR3 indicates current in load 28 of less than desired minimum (1.5 ma) and indicates that load impedance is undesirably high. Brightness of CR4 equal to or greater than reference brightness CR3 indicates that at least 1.5 ma iontophoretic current is being delivered to the load but not greater than 2.0 ma which is controlled by constant current circuit 26.

The present invention is useful in the operation of any iontophoretic device, since overcoming skin impedance is a major problem in successful drug delivery. While the invention has been illustrated in terms of a test device which iontophoretically drives pilocarpine into the skin, it is to be understood that this embodiment is not limiting as to the scope of the present invention, but merely illustrative.

What is claimed is:

1. A medical device for making iontophoretic contact with skin of a patient comprising:

a first visual indicator having a first controlled indication level;

means for making iontophoretic contact with skin of a patient;

means for measuring current flow across the impedance of the patient's skin;

a second visual indicator;

means for activating the second visual indicator to a indication level indicative of current flow across the impedance of the patient's skin, so that the indication level may be visually compared to the first indication level.

2. The device of claim 1 wherein the first visual indicator and the second visual indicator are lights.

3. In a medical device operating by iontophoretic contact with the skin, the improvement comprising:

a first control light which is constantly illuminated to a control brightness;

means for making iontophoretic contact with skin of a patient;

means for measuring iontophoretic current flow across the impedance of the patient's skin; and means electrically connected to the means for sensing current flow for determining a level of satisfactory current flow; a second indicator light; and means responsive to the means for sensing current flow for illuminating the second light, such that a satisfactory level of current flow results in an illumination of the second light generally visually equivalent to the illumination of the first light.

4. A method of iontophoretic treatment of a human patient comprising the following steps:

providing a device for making iontophoretic contact with the skin;

providing a first light of a constant control brightness;

providing a second light electrically connected with the device for iontophoretic contact such that brightness of a light indicates the quality of the contact with the skin;

comparing the brightness of the second light with the brightness of the first light; and determining, based upon general equivalence of the brightness of the first and second lights that proper iontophoretic contact with the skin has been achieved.

* * * * *